United States Patent
Shetty et al.

(10) Patent No.: US 7,262,704 B2
(45) Date of Patent: Aug. 28, 2007

(54) INFORMATION HANDLING SYSTEM INCLUDING DUST DETECTION

(75) Inventors: Santosh Shetty, Round Rock, TX (US);
Paul T. Artman, Austin, TX (US);
Charlie Sumrell, Austin, TX (US)

(73) Assignee: Dell Products L.P., Round Rock, TX (US)

( * ) Notice: Subject to any disclaimer, the term of this patent is extended or adjusted under 35 U.S.C. 154(b) by 56 days.

(21) Appl. No.: 11/063,361

(22) Filed: Feb. 23, 2005

(65) Prior Publication Data

US 2006/0187458 A1    Aug. 24, 2006

(51) Int. Cl.
*G08B 21/00* (2006.01)
(52) U.S. Cl. .................. 340/627; 340/628; 340/693.6
(58) Field of Classification Search ............... 340/627, 340/628, 629, 630, 506, 3.1, 3.43, 693.6; 714/30, 47
See application file for complete search history.

(56) References Cited

U.S. PATENT DOCUMENTS

| | | | |
|---|---|---|---|
| 6,369,706 B1 * | 4/2002 | Anderson et al. | 340/521 |
| 6,549,129 B2 * | 4/2003 | Anderson et al. | 340/521 |
| 6,628,907 B2 * | 9/2003 | Dinca et al. | 399/98 |
| 6,756,905 B2 | 6/2004 | Rattman et al. | |
| 6,779,380 B1 | 8/2004 | Nieuwkamp | |
| 2004/0031928 A1 * | 2/2004 | Smith | 250/380 |

* cited by examiner

*Primary Examiner*—Toan N. Pham

(74) *Attorney, Agent, or Firm*—Haynes and Boone, LLP

(57) ABSTRACT

An information handling system ("IHS") including an enclosure is provided. A dust detection circuit, located inside the enclosure, is also provided. The dust detection circuit determines whether an amount of dust present inside the enclosure is greater than a predetermined amount.

24 Claims, 4 Drawing Sheets

US 7,262,704 B2

INFORMATION HANDLING SYSTEM INCLUDING DUST DETECTION

BACKGROUND

The description herein relates generally to information handling systems ("IHSs") and more particularly to detecting dust within an IHS.

As the value and use of information continues to increase, individuals and businesses seek additional ways to process and store information. One option is an information handling system ("IHS"). An IHS generally processes, compiles, stores, and/or communicates information or data for business, personal, or other purposes. Because technology and information handling needs and requirements may vary between different applications, IHSs may also vary regarding what information is handled, how the information is handled, how much information is processed, stored, or communicated, and how quickly and efficiently the information may be processed, stored, or communicated. The variations in IHSs allow for IHSs to be general or configured for a specific user or specific use such as financial transaction processing, airline reservations, enterprise data storage, or global communications. In addition, IHSs may include a variety of hardware and software components that may be configured to process, store, and communicate information and may include one or more computer systems, data storage systems, and networking systems.

An IHS generally includes various components (e.g., a processor, a memory, a chipset, and other micro devices) located on its system board. While the IHS is operating, its components are capable of generating heat. For such components, capacity for heat transfer (e.g., heat dissipation) is important. In one example, a processor's heat sink with reduced capacity for heat transfer may cause various problems, such as reduced reliability and/or performance associated with processor throttling and increased fan speed.

Heat transfer capacity for a component of an IHS is a function of the convective heat transfer coefficient of the component's heat transfer surface. For example, heat generated by a component is removed via it's heat transfer surface to heat transfer media (e.g., air). Dust, capable of accumulating in the IHS' enclosure, is an insulator between the component's heat transfer surface and the air. Accordingly, dust inside the IHS' enclosure may reduce the component's heat transfer coefficient and, thus, its heat transfer capacity.

What is needed is an IHS that detects dust, without the disadvantages discussed above.

SUMMARY

Accordingly, an information handling system ("IHS") including an enclosure is provided. Also, a dust detection circuit, located inside the enclosure, is provided. The dust detection circuit determines whether an amount of dust present inside the enclosure is greater than a predetermined amount.

DETAILED DESCRIPTION

For purposes of this disclosure, an information handling system ("IHS") may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, entertainment, or other purposes. For example, an IHS may be a personal computer, a personal digital assistant ("PDA"), a consumer electronic device, a network server or storage device, a switch router or other network communication device, or any other suitable device and may vary in size, shape, performance, functionality, and price. The IHS may include memory, one or more processing resources such as a central processing unit ("CPU") or hardware or software control logic. Additional components of the IHS may include one or more storage devices, one or more communications ports for communicating with external devices as well as various input and output (I/O) devices, such as a keyboard, a mouse, and a video display. The IHS may also include one or more buses operable to transmit communications between the various hardware components.

Figure 1:
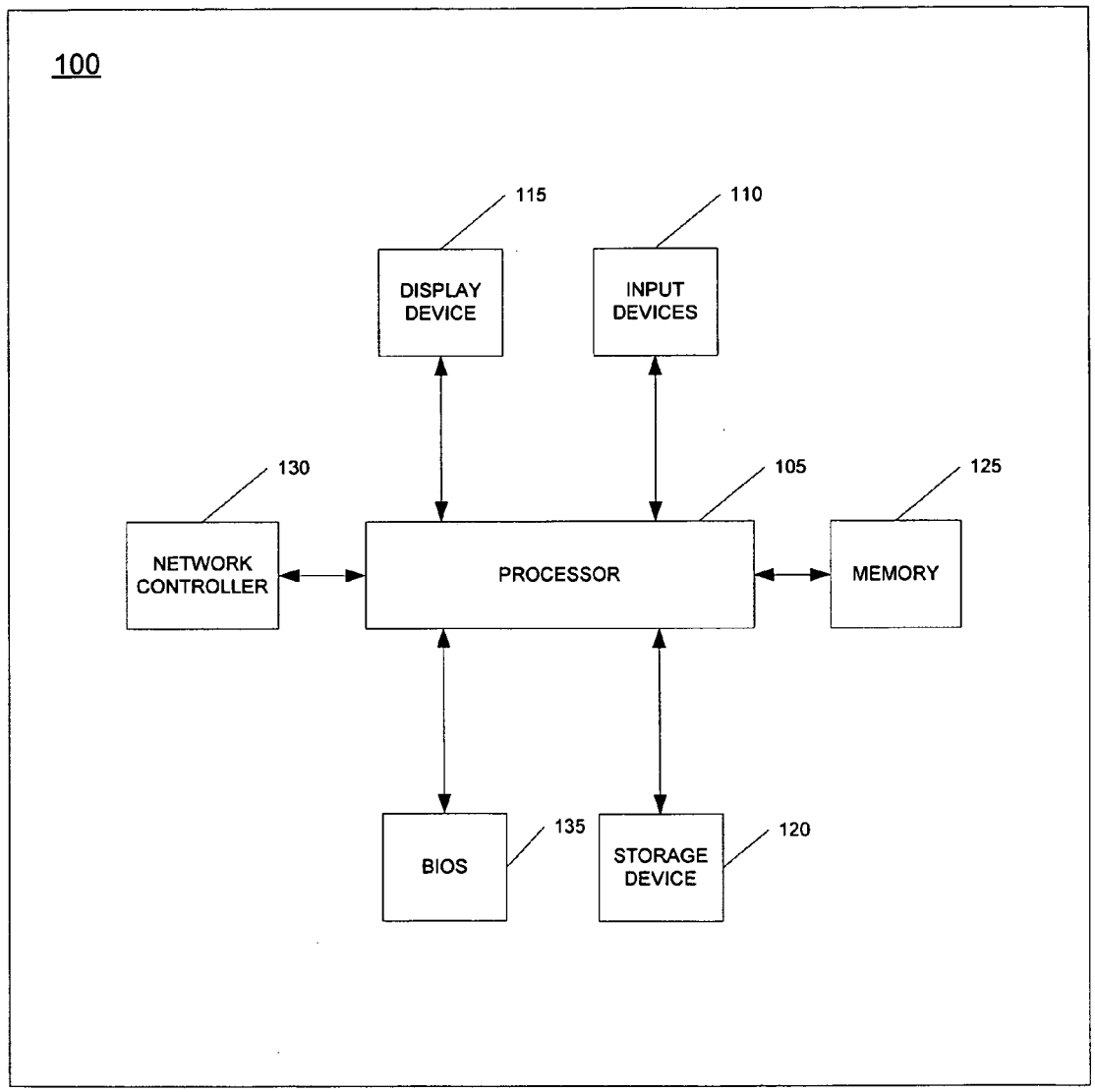
FIG. 1 is a block diagram of an information handling system according to an illustrative embodiment.

FIG. 1 is a block diagram of an IHS, indicated generally at 100, according to the illustrative embodiment. The IHS 100 includes a processor 105 (e.g., an Intel Pentium series processor) for executing and otherwise processing instructions, input devices 110 for receiving information from a human user, a display device 115 (e.g., a cathode ray tube ("CRT") device, a projector, a liquid crystal display ("LCD") device, or a plasma display device) for displaying information to the user, a storage device 120 (e.g., a non-volatile storage device such as a hard disk drive or other computer readable medium or apparatus) for storing information, a memory device 125 (e.g., random access memory ("RAM") device and read only memory ("ROM") device), also for storing information, and a network controller 130 for communicating between the IHS 100 and a network. Each of the input devices 110, the display device 115, the storage device 120, the memory device 125, and the network controller 130 is coupled to the processor 105, and to one another. In one example, the IHS 100 includes various other electronic circuitry for performing other operations of the IHS 100, such as a print device (e.g., a ink-jet printer or a laser printer) for printing visual images on paper.

The input devices 110 include, for example, a conventional keyboard and a pointing device (e.g., a "mouse", a roller ball, or a light pen). A user operates the keyboard to input alphanumeric text information to the processor 105, and the processor receives such information from the keyboard. A user also operates the pointing device to input cursor-control information to the processor 105, and the processor 105 receives such cursor-control information from the pointing device.

The IHS 100 also includes a basic input/output system ("BIOS") 135. The BIOS 135 includes instructions executed by the processor 105, so that the IHS 100 is capable of performing basic operations without executing instructions (e.g., instructions included by an operating system ("OS") stored by the storage device 120. In one example the BIOS 135 is stored in a ROM (e.g., the memory device 125).

Figure 2:
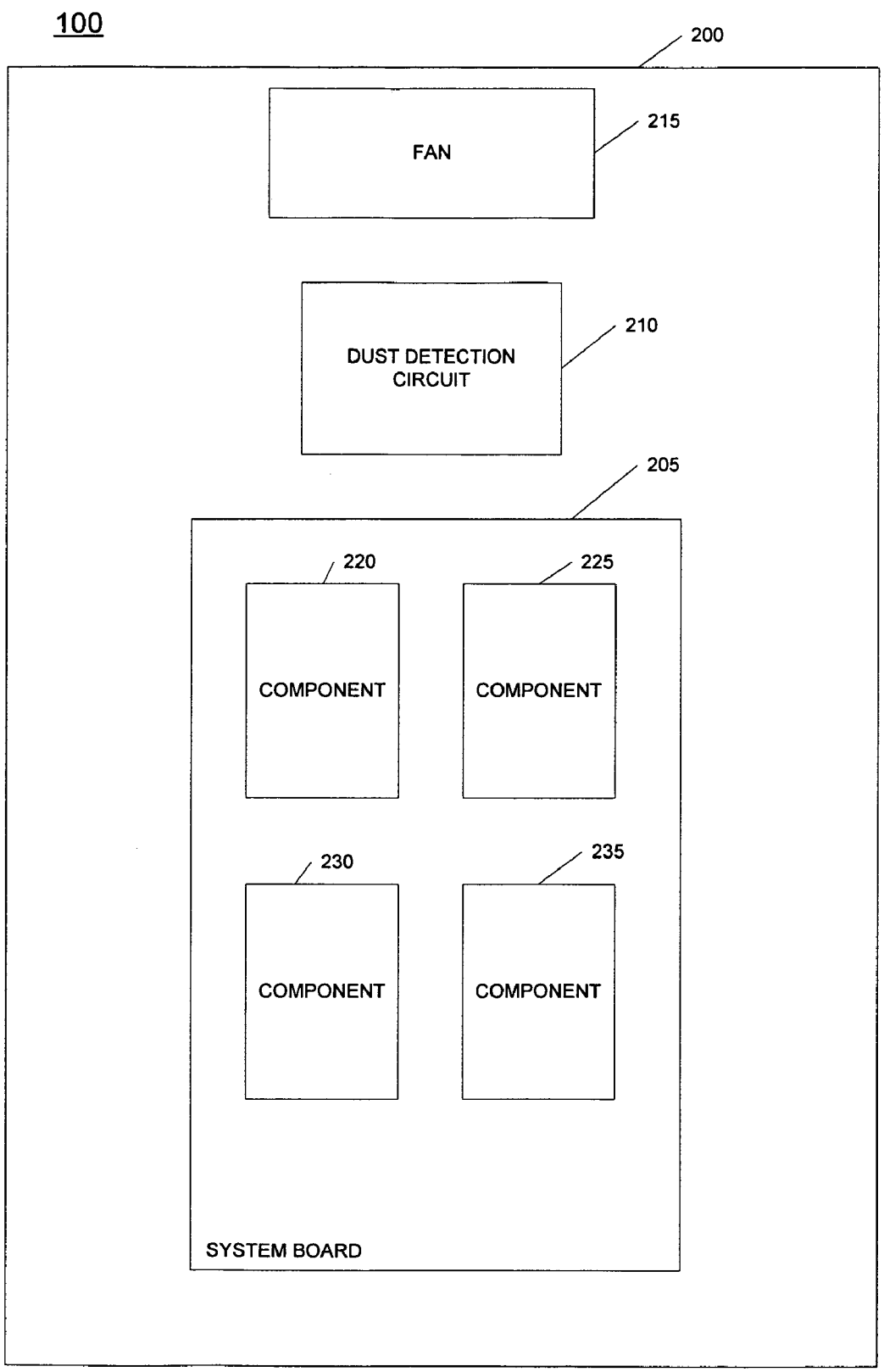
FIG. 2 is another block diagram of the information handling system of FIG. 1.

FIG. 2 is another block diagram of the IHS 100 of FIG. 1, according to the illustrative embodiment. The IHS 100 includes an enclosure (e.g., a case) 200. The enclosure 200 includes a system board 205. The system board 205 includes components 220, 225, 230, and 235. Examples of the components 220, 225, 230, and 235 include a processor (e.g., the processor 105), a memory (e.g., the memory 125), and a chipset. For clarity, FIG. 2 shows only the four components 220, 225, 230, and 235, although the system board 205 may include additional components (e.g., additional processors or additional memories).

The enclosure 200 of the IHS 100 also includes a dust detection circuit 210 for detecting dust as discussed in more detail below (in connection with FIG. 2). Moreover, the enclosure 200 includes a fan 215 for drawing air from outside and circulating air inside the enclosure 200.

As discussed above, presence of dust inside an enclosure of the IHS 100, may reduce the IHS' components' heat transfer capacity. The fan 215 contributes to accumulation of dust inside the enclosure 200 by drawing dust along with air from outside and circulating such dust inside the enclosure 200. By circulating dust inside the enclosure 200, the fan causes dust accumulation on the system board 205 and the components 220, 225, 230, and 235.

As shown in FIG. 2, the dust detection circuit 210 is located proximate the system board 205 so that the dust detection circuit 210 is capable of determining whether heat transfer capacities of the components 220, 225, 230, and 235 are reduced because of dust accumulation. In one example, the dust detection circuit 210 is also located proximate the fan 215.

The dust detection circuit 210 determines whether heat transfer capacities of such components 220, 225, 230, and 235 are reduced by determining whether an amount of dust present inside the enclosure 200 is greater than a previously determined amount (e.g., a threshold amount). Such previously determined amount is variable for different IHSs and components. In the illustrative embodiment, the previously determined amount is determined by measuring an amount of dust accumulation that sufficiently reduces a component's heat transfer capacity so that the component's performance or reliability is also reduced.

Figure 3:
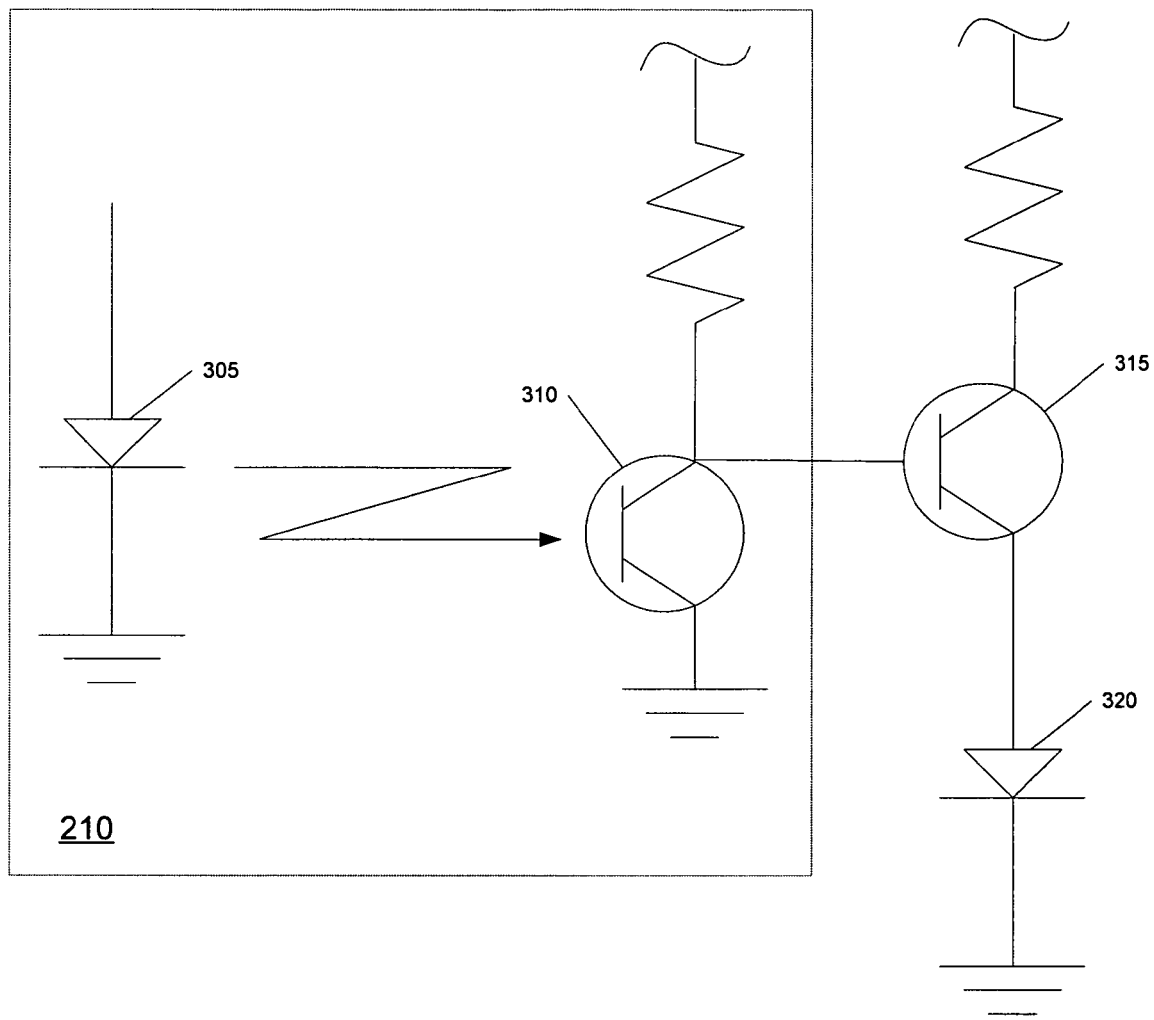
FIG. 3 is a block diagram of a dust detection circuit of FIG. 2.

FIG. 3 is a block diagram of the dust detection circuit 210 of FIG. 2 according to an illustrative embodiment. The dust detection circuit 210 includes a light source 305 and an optical sensor 310. In the illustrative embodiment, the light source 305 is a light emitting diode ("LED") and the optical sensor 310 is an optical transistor.

The optical sensor 310 is coupled to an indicator device 320 via a transistor 315. In the illustrative embodiment, the indicator device 320 is a LED. However, in other embodiments, the indicator device 320 is any device, such as a visual or an audio device suitable for indicating to a user that an amount of dust present inside the enclosure 200 is above a previously determined amount.

Figure 4:
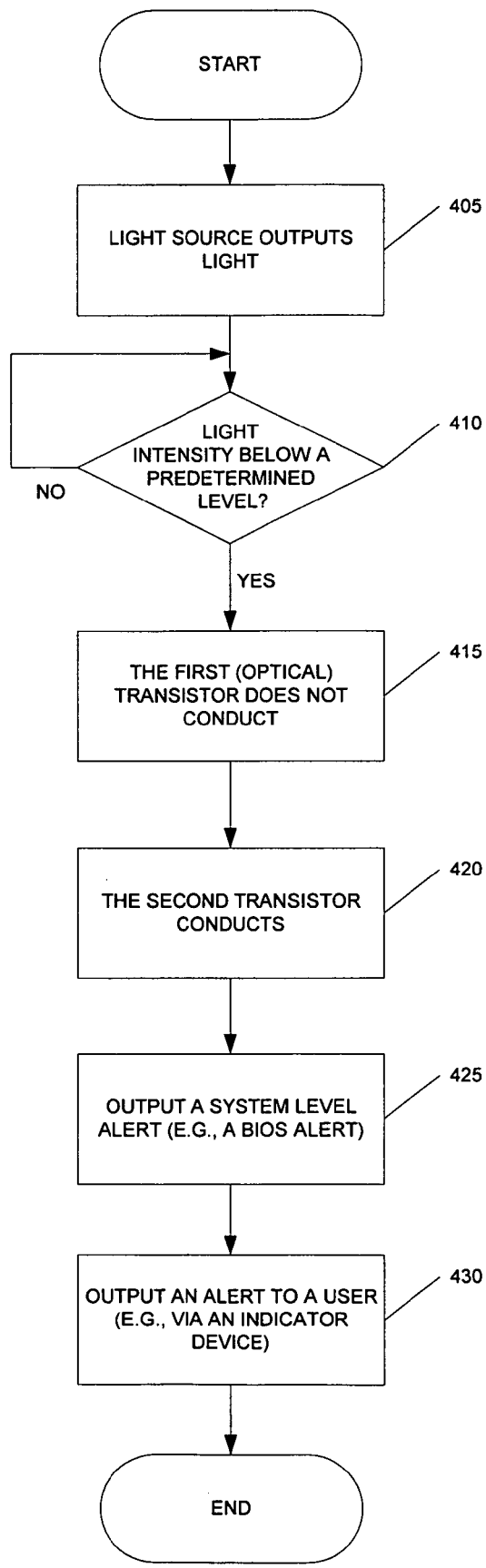
FIG. 4 is a flow chart of operations performed by the dust detection circuit of FIG. 3.

For clarity, the following discussion references both FIG. 3 and FIG. 4. Also for clarity, the following discussion references the optical sensor 310 as being an optical transistor. FIG. 4 is a flow chart of operations performed by the dust detection circuit of FIG. 3, for detecting dust, according to the illustrative embodiment. The operation begins at a step 405, where the light source 305 outputs light. In one example, the light source 305 outputs light in a continuous manner. However, in an alternative embodiment, the light source 305 outputs light intermittently.

The optical transistor 310 is capable of receiving such light output by the light source 305. Intensity of light received by the optical transistor 310 from the light source 305 is variable in response to an amount of dust between the light source 305 and the optical transistor 310. Such intensity of light decreases as the amount of dust increases. After the step 405, the operation continues to a step 410.

At the step 410, the optical transistor 310 awaits until intensity of light it receives is below a previously determined level of intensity. Such previously determined level of intensity is associated with the previously determined amount of dust accumulation discussed above (in connection with FIG. 2). Accordingly, the optical transistor 310's receiving light with intensity level that is less than the previously determined level of intensity, is an indication that the amount of dust present between the light source 305 and the optical transistor 310 is sufficient to reduce one or more components' (e.g., the components of FIG. 2) performance and/or reliability. If intensity of light received by the optical transistor 310 is below the previously determined level, the operation continues to a step 415.

At the step 415, the optical transistor 310 does not conduct (e.g., no longer conducts because intensity of light received by the transistor 310 is below the previously determined level). After the step 415, the operation continues to a step 420.

At the step 420, because the optical transistor 310 no longer conducts (e.g., no longer conducts with ground), the transistor 315 conducts. After the step 420, the operation continues to a step 425.

At the step 425, the transistor 315's conducting causes a system level alert. In one example, such system level alert is a BIOS alert. After the step 425, the operation continues to a step 430.

At the step 430, the transistor 315's conducting causes the indicator device 320 to activate (e.g., power on). In the illustrative embodiment, the indicator device 320 is a LED which outputs light, visually indicating to a user that an amount of dust accumulation inside the enclosure 200 is greater than a previously determined amount (e.g., a threshold amount or an acceptable amount). In another embodiment, the indicator device 320 is an audio device (e.g., a speaker) that audibly indicates to a user.

Although illustrative embodiments have been shown and described, a wide range of modification, change and substitution is contemplated in the foregoing disclosure. Also, in some instances, some features of the embodiments may be employed without a corresponding use of other features. Accordingly, it is appropriate that the appended claims be construed broadly and in manner consistent with the scope of the embodiments disclosed herein.

What is claimed is:

1. A method for detecting dust accumulation on a heat transfer component comprising:
    providing an information handling system ("IHS") including an enclosure;
    providing a heat transfer component in the enclosure; and
    providing a dust detection circuit, located inside the enclosure, that determines whether an amount of dust accumulated on the heat transfer component is greater than a predetermined amount sufficient to affect the heat transfer capability of the component.

2. The method of claim 1, and comprising:
    in response to determining that the amount of accumulated dust is greater than the predetermined amount, outputting an indication of alert.

3. The method of claim 1, wherein the dust detection circuit is located proximate the IHS' system board.

4. The method of claim 3, wherein the dust detection circuit is located proximate the heat transfer component included on the system board.

5. The method of claim 4, wherein the component is a processor.

6. The method of claim 1, wherein the dust detection circuit is located proximate a fan included in the enclosure.

7. The method of claim 1, wherein the dust detection circuit includes a light source and an optical sensor.

8. The method of claim 7, wherein the light source is a light emitting diode ("LED").

9. The method of claim 7, wherein the optical sensor is an optical transistor.

10. The method of claim 1, wherein the predetermined amount is associated with an amount of dust capable of reducing the heat transfer component's performance.

11. The method of claim 1, wherein the predetermined amount is associated with an amount of dust capable of reducing the heat transfer component's reliability.

12. An information handling system ("IHS") comprising:
   an enclosure;
   a heat transfer component in the enclosure;
   a system board, including a processor, located inside the enclosure; and
   a dust detection circuit, located inside the enclosure, for:
      determining whether an amount of dust accumulated on the heat transfer component is greater than a predetermined amount sufficient to affect the heat transfer capabilities of the component.

13. The IHS of claim 12, wherein the dust detection circuit includes:
   a light source; and
   an optical sensor for receiving light from the light source, and in response to determining that an intensity of light received from the light source is less than a predetermined intensity, determining that an amount of dust is greater than a predetermined amount.

14. The IHS of claim 13, wherein the light source is a light emitting diode ("LED").

15. The IHS of claim 13, wherein the optical sensor is an optical transistor.

16. The IHS of claim 12, and comprising:
   an indicator device for, in response to the dust detection circuit determining that the amount of dust accumulated on the heat transfer component is greater than the predetermined amount, outputting an indication of alert.

17. The IHS of claim 16, wherein the indicator device is a visual device.

18. The IHS of claim 17, wherein the indicator is a LED.

19. The IHS of claim 12, wherein the dust detection circuit is located proximate the system board.

20. The IHS of claim 19, wherein the dust detection circuit is located proximate the heat transfer component included on the system board.

21. The IHS of claim 20, wherein the heat transfer component is the processor.

22. The IHS of claim 12, and comprising:
   a fan, wherein the dust detection circuit is located proximate the fan.

23. The IHS of claim 12, wherein the predetermined amount is associated with an amount of dust capable of reducing the heat transfer component's performance.

24. The IHS of claim 12, wherein the predetermined amount is associated with an amount of dust capable of reducing the heat transfer component's reliability.

* * * * *